United States Patent [19]
Eibl et al.

[11] 3,975,246
[45] Aug. 17, 1976

[54] METHOD OF DISINFECTING WATER

[75] Inventors: Volker Eibl; August Reis, both of Munich, Germany

[73] Assignee: Sachs-Systemtechnik GmbH, Schweinfurt am Main, Germany

[22] Filed: Aug. 12, 1975

[21] Appl. No.: 604,038

Related U.S. Application Data

[63] Continuation-in-part of Ser. No. 473,376, May 28, 1974, abandoned.

[30] Foreign Application Priority Data

June 9, 1973   Germany............................ 2329629

[52] U.S. Cl................................ 204/151; 204/130; 204/180 P
[51] Int. Cl.².......................................... C02B 1/82
[58] Field of Search................ 204/151, 149, 180 P, 204/130; 210/62, 64

[56] References Cited
UNITED STATES PATENTS

| | | | |
|---|---|---|---|
| 2,046,467 | 7/1936 | Krause | 204/24 |
| 2,882,210 | 4/1959 | Jenks | 204/151 |
| 3,600,286 | 8/1971 | Sabins | 204/149 |

*Primary Examiner*—John H. Mack
*Assistant Examiner*—A. C. Prescott
*Attorney, Agent, or Firm*—Hans Berman

[57] ABSTRACT

Anodic disinfection of drinking water by electric current is enhanced when the electrolytic cell is divided into anode and cathode compartments by a membrane permeable to anions, the water to be disinfected is pumped through the anode compartment, and the electrolyte in the cathode compartment is enriched with chlorides, hydroxides, carbonates, or peroxides of the alkali metals, with hydrogen chloride, or with hydrogen peroxide.

10 Claims, 1 Drawing Figure

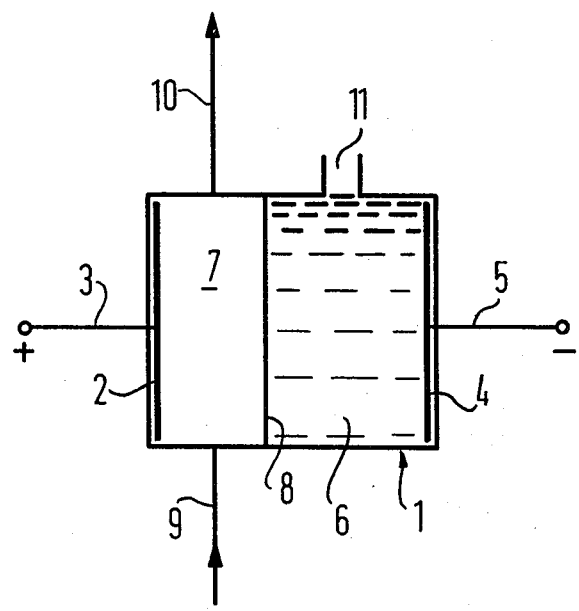

METHOD OF DISINFECTING WATER

This application is a continuation-in-part of our co-pending application Ser. No. 473,376, filed May 28, 1974, and now abandoned.

It is known that microorganisms present in water are destroyed at the anode of an electrolytic cell through which the water flows, if the water contains chlorides. The chlorine generated at the anode acts approximately in the same manner as chlorine liberated by other means, as by decomposition of hypochlorites. The disinfecting action is relatively slow, and it is impossible by the known procedure to avoid an excess of chlorine in the treated water which impairs the taste of the same.

It has now been found that microorganisms in water can be destroyed by electrolysis without impairing the taste of the water and without leaving in the water detectable traces of the chemicals employed during electrolysis.

According to the invention, the water to be disinfected is supplied to the anode compartment of an electrolytic cell divided into an anode compartment and a cathode compartment by a membrane permeable to anions and having electrodes in the compartments. The cathode compartment is provided with an aqueous solution of a chloride, hydroxide, carbonate, or peroxide of an alkali metal, with hydrogen chloride, or with hydrogen peroxide in a concentration which exceeds the concentration of the same compound in the treated water. When direct current is passed between the anode and cathode through the cell, the water withdrawn from the anode compartment shows a disinfecting effect greater than would be observed in the absence of the chemicals dissolved in the catholyte, and the chemicals cannot be detected in the withdrawn, treated water by any change in the taste of the water.

The electrolytic cell employed must be constructed of materials inert to the water and the chemicals so that contamination of the treated water by corrosion products is avoided, but is otherwise not of critical importance. The anode and cathode compartments may be separated by any membrane permeable to anions, but fastest disinfection has been achieved so far with a membrane practically impermeable to cations.

The mechanism of the invention is incompletely understood at this time. The supply of chlorine or hydroxyl ions to the anode compartment is restricted by the membrane separating the compartments, and this feature may account for the absence of residual chemicals in the treated water. It cannot account satisfactorily for the faster disinfecting action achieved as compared to the direct addition of chlorine, hydrogen peroxide, or ozone to the treated water in amounts much larger than can become available in this invention. No adequate explanation is available at this time for the effectiveness of hydrogen peroxide added to a catholyte separated from the anode compartment by a membrane permeable to anions or selectively permeable to anions only.

The current density in the treated water affects the rate of disinfection in a predictable manner, but is not otherwise critical. At excessive current densities, oxygen is liberated at the anode and reduces the current efficiency of the process.

Other features and many of the attendant advantages of this invention will readily be appreciated as the same becomes better understood by reference to the following detailed description of preferred embodiments when considered in connection with the appended drawing whose sole FIGURE illustrates apparatus for performing the method of the invention by conventional symbols.

The apparatus includes a glass cell 1 of generally rectangular shape. Two opposite, parallel walls of the cell are completely covered by an anode sheet 2 of austenitic stainless steel of Type V4A (chromium-nickel-molybdenum steel) and a cathode sheet 4 of Type V2A stainless steel (chromium-nickel steel) respectively. Each electrode has an effective exposed face 6 cm square.

Leads 3, 5 connect the electrodes 2, 4 to the positive and negative terminals of a rectifier. The catholyte in a cell compartment 6 adjacent the cathode 4 is separated by a membrane 8 selectively permeable to anions from the anolyte in a compartment 7 bounded by the anode 3. The discharge pipe 9 of a circulating pump, not otherwise shown, is connected to the anode compartment 7, and an overflow line 10 releases excess liquid from the anode compartment 7. A tubulure 11 permits the liquid in the cathode compartment 6 to be replenished or replaced.

In an actual embodiment of the illustrated cell, the membrane 8 had a thickness of 0.3 mm. It was spaced 4 mm from the parallel, exposed face of the anode 2 and 11 mm from the exposed face of the cathode 4.

The cell was employed in testing the effects of catholyte composition on the disinfection of contaminated drinking water which was pumped through the anode compartment 7. To permit proper evaluation of the tested variables, the same drinking water having a specific conductivity of 0.000420 mhos/cm and artificially contaminated with $10^7$ cells of B. coli per ml prior to each test was pumped through the cell in a closed circuit at a flow rate of 6.25 ml/sec. The potential applied to the electrodes was set at 4 to 7 volts as needed to maintain a current density of 2.7 mA/cm$^2$ at the anode surface. Drops of the circulated drinking water were inoculated from time to time on nutrient agar plates, and the colonies developing within 3 days at 37°C were counted. Graphic evaluation of the culturing tests permitted a fairly precise determination of the dwell time in the cell 1 required to destroy all coli bacteria present, or to reduce them to a desired maximum number.

The necessary dwell time was found to be affected under otherwise equal conditions by the chemical nature and concentration of the electrolyte in the cathode compartment 6 and by the nature of the membrane 8. When the cathode compartment 6 was filled with 0.5% sodium chloride solution, all coli bacteria were killed in drinking water in the anode compartment 7 within 7 seconds when the membrane was a commercially available semipermeable membrane (PERMAPLEX, delivered by Serva, Heidelberg, Germany), and within 42 seconds through a dialysis membrane of regenerated cellulose.

When the cathode compartment 6 was filled with a 1% solution of hydrogen peroxide, all coli bacilli in the circulating anolyte were killed within 50 seconds, using the semipermeable membrane mentioned above.

Adequate, though slower rates of disinfection were achieved with lower concentrations of sodium chloride and hydrogen peroxide, as little as 0.05% sodium chloride in the catholyte being sufficient distinctly to enhance the bactericidal effect of current as compared to an arrangement in which the catholyte consisted of the same drinking water as the anolyte.

When sodium chloride was used in the catholyte, sodium hydroxide gradually accumulated in the cathode compartment, and the catholyte had to be replaced from time to time if constant operating conditions were to be maintained. This could be avoided by using hydrochloric acid instead of sodium chloride. Under otherwise identical conditions, a catholyte containing 0.31% HCl was found to have the same enhanced disinfecting action as the equimolecular 0.5% solution of NaCl described above, and 0.03% HCl was as effective as 0.05% NaCl, all percentage values being by weight.

When a 0.5% sodium hydroxide solution was employed as the catholyte, the contaminated drinking water required a dwell time of 30 – 60 seconds in the anode compartment for complete disinfection, the shorter dwell time being employed with the semipermeable membrane, the longer period with the cellulose membrane.

Limited tests indicated equivalence of potassium chloride and potassium hydroxide with the corresponding sodium compounds for equal concentrations, and similar effectiveness for sodium peroxide, and sodium bicarbonate.

It is characteristic of the disinfecting action of the strongly ionizing compounds enumerated above, such as sodium hydroxide, sodium chloride, hydrogen chloride, or potassium chloride, that they reduce the concentration of pathogenic or other germs in the treated drinking water to zero in a period of less than 1 minute even with a cellulose membrane. When the catholyte is not enriched with ions, as by filling the cathode compartment 6 with the same drinking water that is to be disinfected, the colony count in culture media inoculated with the circulating anolyte drops slowly and ultimately reaches a stable value, much higher than reported above with reference to hydrogen peroxide. We have not succeeded in completely disinfecting the B. coli contaminated drinking water referred to above in the apparatus and under the operating conditions described without enriching the catholyte even when the dwell time was extended to the limits practically available.

The disinfected drinking water was found free of any taste imparted thereto by the catholyte. No free chlorine could be detected in the effluent when the catholyte contained chlorine ions.

The width of the anode compartment between the anode 2 and the membrane 8 has been found to have a significant effect on the rate at which the anolyte is disinfected. The efficiency of the cell is enhanced greatly by passing the liquid to be disinfected over the anode surface in as thin a layer as is practically possible. Passage of liquid through portions of the anode compartment in which the current density is low is to be avoided. Therefore, the anode should be sealed to the cell walls in such a manner as to prevent liquid flow along the anode face directed away from the cathode 4 and the membrane 8.

The potential applied to the electrodes 2, 4 affects the current density at the anode surface, and thereby the disinfecting rate. A potential of at least 1.5 volt should be applied to the electrodes to assure the production of oxygen in statu nascendi at the anode surface, since oxygen generated at the anode seems to play an important role in the disinfecting process. But a potential of 4 to 7 volts is generally most advantageous, and a dwell time of 7 to 150 seconds usually adequate.

What is claimed is:

1. A method of disinfecting water which comprises:
   a. supplying the water to be disinfected to the anode compartment of an electrolytic cell, the cell being divided into said anode compartment and a cathode compartment by a membrane permeable to anions and having an anode and a cathode in said compartments respectively;
   b. maintaining in said cathode compartment an aqueous solution of a member of the group consisting of the chloride, hydroxide, carbonate, and peroxide of an alkali metal, hydrogen chloride, and hydrogen peroxide;
   c. passing direct current between said anode and said cathode through said cell; and
   d. withdrawing disinfected water from said anode compartment,
      1. the concentration of said member in said aqueous solution being greater than the concentration thereof in the water in said anode compartment and sufficient to enhance the disinfecting effect of said current on said water in the anode compartment as compared to the disinfecting effect of said current on said water in the anode compartment when said cathode compartment is filled with said water.

2. A method as set forth in claim 1, wherein said alkali metal is sodium or potassium.

3. A method as set forth in claim 1, wherein said member is sodium chloride, hydrogen chloride, or hydrogen peroxide.

4. A method as set forth in claim 1, wherein a potential difference of at least 1.5 volts is applied to said anode and to said cathode for causing said passing of said direct current.

5. A method as set forth in claim 1, wherein said water to be disinfected contains pathogenic germs when supplied to said anode compartment, and is held in said anode compartment for a period sufficient to kill said germs.

6. A method as set forth in claim 5, wherein said period is 7 seconds to 150 seconds, preferably 7 to 60 seconds.

7. A method as set forth in claim 1, wherein said member is sodium chloride, and said concentration thereof is between 0.05 and 0.5% by weight.

8. A method as set forth in claim 1, wherein said member is hydrogen chloride, and said concentration thereof is between 0.03 and approximately 0.3% by weight.

9. A method as set forth in claim 1, wherein said member is hydrogen peroxide, and said concentration thereof is approximately 1% by weight.

10. A method as set forth in claim 1, wherein said membrane is a semi-permeable membrane selectively permeable to anions only.

* * * * *